(12) United States Patent
Do et al.

(10) Patent No.: US 12,416,634 B2
(45) Date of Patent: Sep. 16, 2025

(54) SNAP-25 REPORTER CONSTRUCTS AND METHODS OF USING THE SAME

(71) Applicant: Galderma Holding S.A., La Tour-de-Peilz (CH)

(72) Inventors: Anh-Tri Do, Uppsala (SE); Robert Fredriksson, Uppsala (SE); Helgi B. Schiöth, Uppsala (SE); Jörgen Jonsson, Uppsala (SE); Michael Williams, Knivsta (SE); Emilia Lekholm, Uppsala (SE)

(73) Assignee: Galderma Holding SA, Zug (CH)

( * ) Notice: Subject to any disclaimer, the term of this patent is extended or adjusted under 35 U.S.C. 154(b) by 1023 days.

(21) Appl. No.: 17/334,119

(22) Filed: May 28, 2021

(65) Prior Publication Data

US 2021/0373021 A1 Dec. 2, 2021

Related U.S. Application Data

(60) Provisional application No. 63/033,007, filed on Jun. 1, 2020.

(51) Int. Cl.
| | |
|---|---|
| *G01N 33/573* | (2006.01) |
| *C07K 14/47* | (2006.01) |
| *C07K 14/82* | (2006.01) |

(52) U.S. Cl.
CPC .......... *G01N 33/573* (2013.01); *C07K 14/47* (2013.01); *C07K 14/82* (2013.01); *C12Y 304/24069* (2013.01); *C07K 2319/00* (2013.01); *G01N 2333/952* (2013.01); *G01N 2470/04* (2021.08)

(58) Field of Classification Search
CPC ........ C12Y 304/24069; C07K 2319/41; C07K 2319/43
See application file for complete search history.

(56) References Cited

U.S. PATENT DOCUMENTS

| 8,940,482 B1 | 1/2015 | Oyler et al. |
| 2004/0072270 A1 | 4/2004 | Fernandez-Salas et al. |
| 2007/0243565 A1 | 10/2007 | Williams et al. |

FOREIGN PATENT DOCUMENTS

| WO | WO200032799 A1 * | 6/2000 | |
| WO | WO 200118038 A2 * | 3/2001 | |
| WO | WO-2011161260 A1 * | 12/2011 | ............. A61K 38/17 |

OTHER PUBLICATIONS

Rust et al (Botulinum neurotoxin type C protease induces apoptosis in differentiated human neuroblastoma cells. Oncotarget. May 31, 2016;7(22):33220-8. doi: 10.18632/oncotarget.8903) (Year: 2016).*

Roberts et al(The inhibitor of apoptosis protein-binding domain of Smac is not essential for its proapoptotic activity. J Cell Biol. Apr. 2, 2001;153(1):221-8. doi: 10.1083/jcb.153.1.221) (Year: 2001).*

Dorner et al., "Complexity of botulinum neurotoxins: challenges for detection technology.", Botulinum Neurotoxins, vol. 364, 2012, pp. 219-255 (37 pages).

International Search Report and Written Opinion issued for PCT Appl. Ser. No. PCT/IB2021/054725 dated Dec. 13, 2021 (22 pages).

Tsai et al., "Targeting botulinum neurotoxin persistence by the ubiquitin-proteasome system." Proceedings of the National Academy of Sciences, vol. 107, No. 38, 2010, pp. 16554-16559 (6 pages).

* cited by examiner

*Primary Examiner* — Gregory S Emch
*Assistant Examiner* — Ashley H. Gao
(74) *Attorney, Agent, or Firm* — Sunit Talapatra; Foley & Lardner LLP

(57) ABSTRACT

The present disclosure relates generally to peptide reporter constructs of SNAP-25, which are useful in determining the activity of *botulinum* toxins, and methods of using the same.

28 Claims, 8 Drawing Sheets

Specification includes a Sequence Listing.

FIG. 1

A. SNAP-25 Reporter 1 [MYC] [SNAP-25 1-197] [-206] SEQ ID NO: 9

MEQKLSEEDLAEDADMRNELEEMQRRADQLADESLESTRRMLQLVEESKDAGIRTLVMLDEQGEQLERIEEGM
DQINKDMKEAEKNLTDLGKFCGLCVCPCNKLKSSDAYKKAWGNNQDGVVASQPARVVDEREQMAISGGFIRRV
TNDARENEMDENLEQVSGIIGNLRHMALDMGNEIDTQNRQIDRIMEKADSNKTRIDEANQRATKMLGSG

B. SNAP-25 Reporter 2 [MYC] [SNAP-25 1-197] [-206] [DIABLO] SEQ ID NO: 10

MEQKLSEEDLAEDADMRNELEEMQRRADQLADESLESTRRMLQLVEESKDAGIRTLVMLDEQGEQLERIEEGM
DQINKDMKEAEKNLTDLGKFCGLCVCPCNKLKSSDAYKKAWGNNQDGVVASQPARVVDEREQMAISGGFIRRV
TNDARENEMDENLEQVSGIIGNLRHMALDMGNEIDTQNRQIDRIMEKADSNKTRIDEANQRATKMLGSGAVPIAQK

C. SNAP-25 Reporter 3 [MYC] [SNAP-25 1-197] [DIABLO] SEQ ID NO: 11

MEQKLSEEDLAEDADMRNELEEMQRRADQLADESLESTRRMLQLVEESKDAGIRTLVMLDEQGEQLERIEEGM
DQINKDMKEAEKNLTDLGKFCGLCVCPCNKLKSSDAYKKAWGNNQDGVVASQPARVVDEREQMAISGGFIRRV
TNDARENEMDENLEQVSGIIGNLRHMALDMGNEIDTQNRQIDRIMEKADSNKTRIDEANQAVPIAQK

D. SNAP-25 Reporter 4 [MYC] [SNAP-25 1-197] [-206] [DIABLO] SEQ ID NO: 12

MEQKLSEEDLAEDADMRNELEEMQRRADQLADESLESTRRMLQLVEESKDAGIRTLVMLDEQGEQLERIEEGM
DQINKDMKEAEKNLTDLGKFCGLCVCPCNKLKSSDAYKKAWGNNQDGVVASQPARVVDEREQMAISGGFIRRV
TNDARENEMDENLEQVSGIIGNLRHMALDMGNEIDTQNRQIDRIMEKADSNKTRIDEANQRATKMLGSGAVPIAQK

E. SNAP-25 Reporter 5 [MYC] [SNAP-25 1-197] [DIABLO] SEQ ID NO: 13

MEQKLSEEDLAEDADMRNELEEMQRRADQLADESLESTRRMLQLVEESKDAGIRTLVMLDEQGEQLERIEEGM
DQINKDMKEAEKNLTDLGKFCGLCVCPCNKLKSSDAYKKAWGNNQDGVVASQPARVVDEREQMAISGGFIRRV
TNDARENEMDENLEQVSGIIGNLRHMALDMGNEIDTQNRQIDRIMEKADSNKTRIDEANQAVPIAQK

SEQUENCE LISTING

```
<160> NUMBER OF SEQ ID NOS: 15

<210> SEQ ID NO 1
<211> LENGTH: 197
<212> TYPE: PRT
<213> ORGANISM: Homo sapiens

<400> SEQUENCE: 1

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45
```

Met Leu Asp Glu Gln Gly Glu Gln Leu Glu Arg Ile Glu Glu Gly Met
        50                      55                      60

Asp Gln Ile Asn Lys Asp Met Lys Glu Ala Glu Lys Asn Leu Thr Asp
65                      70                      75                      80

Leu Gly Lys Phe Cys Gly Leu Cys Val Cys Pro Cys Asn Lys Leu Lys
                        85                      90                      95

Ser Ser Asp Ala Tyr Lys Lys Ala Trp Gly Asn Asn Gln Asp Gly Val
                100                     105                     110

Val Ala Ser Gln Pro Ala Arg Val Val Asp Glu Arg Glu Gln Met Ala
                115                     120                     125

Ile Ser Gly Gly Phe Ile Arg Arg Val Thr Asn Asp Ala Arg Glu Asn
                130                     135                     140

Glu Met Asp Glu Asn Leu Glu Gln Val Ser Gly Ile Ile Gly Asn Leu
145                     150                     155                     160

Arg His Met Ala Leu Asp Met Gly Asn Glu Ile Asp Thr Gln Asn Arg
                165                     170                     175

Gln Ile Asp Arg Ile Met Glu Lys Ala Asp Ser Asn Lys Thr Arg Ile
                180                     185                     190

Asp Glu Ala Asn Gln
                195

<210> SEQ ID NO 2
<211> LENGTH: 206
<212> TYPE: PRT
<213> ORGANISM: Homo sapiens

<400> SEQUENCE: 2

Met Ala Glu Asp Ala Asp Met Arg Asn Glu Leu Glu Glu Met Gln Arg
1               5                       10                      15

Arg Ala Asp Gln Leu Ala Asp Glu Ser Leu Glu Ser Thr Arg Arg Met
                20                      25                      30

Leu Gln Leu Val Glu Glu Ser Lys Asp Ala Gly Ile Arg Thr Leu Val
                35                      40                      45

Met Leu Asp Glu Gln Gly Glu Gln Leu Glu Arg Ile Glu Glu Gly Met
        50                      55                      60

Asp Gln Ile Asn Lys Asp Met Lys Glu Ala Glu Lys Asn Leu Thr Asp
65                      70                      75                      80

Leu Gly Lys Phe Cys Gly Leu Cys Val Cys Pro Cys Asn Lys Leu Lys
                        85                      90                      95

Ser Ser Asp Ala Tyr Lys Lys Ala Trp Gly Asn Asn Gln Asp Gly Val
                100                     105                     110

Val Ala Ser Gln Pro Ala Arg Val Val Asp Glu Arg Glu Gln Met Ala
                115                     120                     125

Ile Ser Gly Gly Phe Ile Arg Arg Val Thr Asn Asp Ala Arg Glu Asn
                130                     135                     140

Glu Met Asp Glu Asn Leu Glu Gln Val Ser Gly Ile Ile Gly Asn Leu
145                     150                     155                     160

Arg His Met Ala Leu Asp Met Gly Asn Glu Ile Asp Thr Gln Asn Arg
                165                     170                     175

Gln Ile Asp Arg Ile Met Glu Lys Ala Asp Ser Asn Lys Thr Arg Ile
                180                     185                     190

Asp Glu Ala Asn Gln Arg Ala Thr Lys Met Leu Gly Ser Gly
                195                     200                     205

```
<210> SEQ ID NO 3
<211> LENGTH: 10
<212> TYPE: PRT
<213> ORGANISM: Homo sapiens

<400> SEQUENCE: 3

Glu Gln Lys Leu Ile Ser Glu Glu Asp Leu
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Tyr Lys Asp Asp Asp Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Tyr Lys Asp Asp Asp Asp Lys
1               5

<210> SEQ ID NO 6
<211> LENGTH: 9
<212> TYPE: PRT
<213> ORGANISM: Homo sapiens

<400> SEQUENCE: 6

Arg Ala Thr Lys Met Leu Gly Ser Gly
1               5

<210> SEQ ID NO 7
<211> LENGTH: 7
<212> TYPE: PRT
<213> ORGANISM: Homo sapiens

<400> SEQUENCE: 7

Ala Val Pro Ile Ala Gln Lys
1               5

<210> SEQ ID NO 8
<211> LENGTH: 7
<212> TYPE: PRT
<213> ORGANISM: Homo sapiens

<400> SEQUENCE: 8

Gln Ala Val Pro Ile Ala Gln
1               5

<210> SEQ ID NO 9
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 9

```
Met Glu Gln Lys Leu Ile Ser Glu Glu Asp Leu Met Ala Glu Asp Ala
1               5                   10                  15

Asp Met Arg Asn Glu Leu Glu Glu Met Gln Arg Arg Ala Asp Gln Leu
            20                  25                  30

Ala Asp Glu Ser Leu Glu Ser Thr Arg Arg Met Leu Gln Leu Val Glu
        35                  40                  45

Glu Ser Lys Asp Ala Gly Ile Arg Thr Leu Val Met Leu Asp Glu Gln
    50                  55                  60

Gly Glu Gln Leu Glu Arg Ile Glu Glu Gly Met Asp Gln Ile Asn Lys
65                  70                  75                  80

Asp Met Lys Glu Ala Glu Lys Asn Leu Thr Asp Leu Gly Lys Phe Cys
                85                  90                  95

Gly Leu Cys Val Cys Pro Cys Asn Lys Leu Lys Ser Ser Asp Ala Tyr
            100                 105                 110

Lys Lys Ala Trp Gly Asn Asn Gln Asp Gly Val Val Ala Ser Gln Pro
            115                 120                 125

Ala Arg Val Val Asp Glu Arg Glu Gln Met Ala Ile Ser Gly Gly Phe
        130                 135                 140

Ile Arg Arg Val Thr Asn Asp Ala Arg Glu Asn Glu Met Asp Glu Asn
145                 150                 155                 160

Leu Glu Gln Val Ser Gly Ile Ile Gly Asn Leu Arg His Met Ala Leu
                165                 170                 175

Asp Met Gly Asn Glu Ile Asp Thr Gln Asn Arg Gln Ile Asp Arg Ile
            180                 185                 190

Met Glu Lys Ala Asp Ser Asn Lys Thr Arg Ile Asp Glu Ala Asn Gln
        195                 200                 205

Arg Ala Thr Lys Met Leu Gly Ser Lys Asp Tyr Lys Asp Asp Asp Lys
    210                 215                 220
```

<210> SEQ ID NO 10
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Glu Gln Lys Leu Ile Ser Glu Glu Asp Leu Met Ala Glu Asp Ala
1               5                   10                  15

Asp Met Arg Asn Glu Leu Glu Glu Met Gln Arg Arg Ala Asp Gln Leu
            20                  25                  30

Ala Asp Glu Ser Leu Glu Ser Thr Arg Arg Met Leu Gln Leu Val Glu
        35                  40                  45

Glu Ser Lys Asp Ala Gly Ile Arg Thr Leu Val Met Leu Asp Glu Gln
    50                  55                  60

Gly Glu Gln Leu Glu Arg Ile Glu Glu Gly Met Asp Gln Ile Asn Lys
65                  70                  75                  80

Asp Met Lys Glu Ala Glu Lys Asn Leu Thr Asp Leu Gly Lys Phe Cys
                85                  90                  95

Gly Leu Cys Val Cys Pro Cys Asn Lys Leu Lys Ser Ser Asp Ala Tyr
            100                 105                 110

Lys Lys Ala Trp Gly Asn Asn Gln Asp Gly Val Val Ala Ser Gln Pro
            115                 120                 125
```

Ala Arg Val Val Asp Glu Arg Glu Gln Met Ala Ile Ser Gly Gly Phe
            130                 135                 140

Ile Arg Arg Val Thr Asn Asp Ala Arg Glu Asn Glu Met Asp Glu Asn
145                 150                 155                 160

Leu Glu Gln Val Ser Gly Ile Ile Gly Asn Leu Arg His Met Ala Leu
                165                 170                 175

Asp Met Gly Asn Glu Ile Asp Thr Gln Asn Arg Gln Ile Asp Arg Ile
            180                 185                 190

Met Glu Lys Ala Asp Ser Asn Lys Thr Arg Ile Asp Glu Ala Asn Gln
        195                 200                 205

Arg Ala Thr Lys Met Leu Gly Ser Gly Ala Val Pro Ile Ala Gln Lys
    210                 215                 220

Asp Tyr Lys Asp Asp Lys
225                 230

<210> SEQ ID NO 11
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Gln Lys Leu Ile Ser Glu Glu Asp Leu Met Ala Glu Asp Ala
1               5                   10                  15

Asp Met Arg Asn Glu Leu Glu Glu Met Gln Arg Arg Ala Asp Gln Leu
            20                  25                  30

Ala Asp Glu Ser Leu Glu Ser Thr Arg Arg Met Leu Gln Leu Val Glu
        35                  40                  45

Glu Ser Lys Asp Ala Gly Ile Arg Thr Leu Val Met Leu Asp Glu Gln
    50                  55                  60

Gly Glu Gln Leu Glu Arg Ile Glu Glu Gly Met Asp Gln Ile Asn Lys
65                  70                  75                  80

Asp Met Lys Glu Ala Glu Lys Asn Leu Thr Asp Leu Gly Lys Phe Cys
                85                  90                  95

Gly Leu Cys Val Cys Pro Cys Asn Lys Leu Lys Ser Ser Asp Ala Tyr
            100                 105                 110

Lys Lys Ala Trp Gly Asn Asn Gln Asp Gly Val Val Ala Ser Gln Pro
        115                 120                 125

Ala Arg Val Val Asp Glu Arg Glu Gln Met Ala Ile Ser Gly Gly Phe
    130                 135                 140

Ile Arg Arg Val Thr Asn Asp Ala Arg Glu Asn Glu Met Asp Glu Asn
145                 150                 155                 160

Leu Glu Gln Val Ser Gly Ile Ile Gly Asn Leu Arg His Met Ala Leu
                165                 170                 175

Asp Met Gly Asn Glu Ile Asp Thr Gln Asn Arg Gln Ile Asp Arg Ile
            180                 185                 190

Met Glu Lys Ala Asp Ser Asn Lys Thr Arg Ile Asp Glu Ala Asn Gln
        195                 200                 205

Ala Val Pro Ile Ala Gln Lys Asp Tyr Lys Asp Asp Lys
    210                 215                 220

<210> SEQ ID NO 12
<211> LENGTH: 224
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 12

Met Glu Gln Lys Leu Ile Ser Glu Glu Asp Leu Met Ala Glu Asp Ala
1               5                   10                  15

Asp Met Arg Asn Glu Leu Glu Glu Met Gln Arg Arg Ala Asp Gln Leu
            20                  25                  30

Ala Asp Glu Ser Leu Glu Ser Thr Arg Arg Met Leu Gln Leu Val Glu
        35                  40                  45

Glu Ser Lys Asp Ala Gly Ile Arg Thr Leu Val Met Leu Asp Glu Gln
    50                  55                  60

Gly Glu Gln Leu Glu Arg Ile Glu Glu Gly Met Asp Gln Ile Asn Lys
65                  70                  75                  80

Asp Met Lys Glu Ala Glu Lys Asn Leu Thr Asp Leu Gly Lys Phe Cys
                85                  90                  95

Gly Leu Cys Val Cys Pro Cys Asn Lys Leu Lys Ser Ser Asp Ala Tyr
            100                 105                 110

Lys Lys Ala Trp Gly Asn Asn Gln Asp Gly Val Val Ala Ser Gln Pro
        115                 120                 125

Ala Arg Val Val Asp Glu Arg Glu Gln Met Ala Ile Ser Gly Gly Phe
    130                 135                 140

Ile Arg Arg Val Thr Asn Asp Ala Arg Glu Asn Glu Met Asp Glu Asn
145                 150                 155                 160

Leu Glu Gln Val Ser Gly Ile Ile Gly Asn Leu Arg His Met Ala Leu
                165                 170                 175

Asp Met Gly Asn Glu Ile Asp Thr Gln Asn Arg Gln Ile Asp Arg Ile
            180                 185                 190

Met Glu Lys Ala Asp Ser Asn Lys Thr Arg Ile Asp Glu Ala Asn Gln
        195                 200                 205

Arg Ala Thr Lys Met Leu Gly Ser Gly Ala Val Pro Ile Ala Gln Lys
    210                 215                 220

<210> SEQ ID NO 13
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Glu Gln Lys Leu Ile Ser Glu Glu Asp Leu Met Ala Glu Asp Ala
1               5                   10                  15

Asp Met Arg Asn Glu Leu Glu Glu Met Gln Arg Arg Ala Asp Gln Leu
            20                  25                  30

Ala Asp Glu Ser Leu Glu Ser Thr Arg Arg Met Leu Gln Leu Val Glu
        35                  40                  45

Glu Ser Lys Asp Ala Gly Ile Arg Thr Leu Val Met Leu Asp Glu Gln
    50                  55                  60

Gly Glu Gln Leu Glu Arg Ile Glu Glu Gly Met Asp Gln Ile Asn Lys
65                  70                  75                  80

Asp Met Lys Glu Ala Glu Lys Asn Leu Thr Asp Leu Gly Lys Phe Cys
                85                  90                  95

Gly Leu Cys Val Cys Pro Cys Asn Lys Leu Lys Ser Ser Asp Ala Tyr

```
                        100                 105                 110
Lys Lys Ala Trp Gly Asn Asn Gln Asp Gly Val Val Ala Ser Gln Pro
            115                 120                 125

Ala Arg Val Val Asp Glu Arg Glu Gln Met Ala Ile Ser Gly Gly Phe
        130                 135                 140

Ile Arg Arg Val Thr Asn Asp Ala Arg Glu Asn Glu Met Asp Glu Asn
145                 150                 155                 160

Leu Glu Gln Val Ser Gly Ile Ile Gly Asn Leu Arg His Met Ala Leu
                165                 170                 175

Asp Met Gly Asn Glu Ile Asp Thr Gln Asn Arg Gln Ile Asp Arg Ile
                180                 185                 190

Met Glu Lys Ala Asp Ser Asn Lys Thr Arg Ile Asp Glu Ala Asn Gln
            195                 200                 205

Ala Val Pro Ile Ala Gln Lys
        210                 215

<210> SEQ ID NO 14
<211> LENGTH: 4
<212> TYPE: PRT
<213> ORGANISM: Homo sapiens

<400> SEQUENCE: 14

Ala Val Pro Ile
1

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Asp Tyr Lys Lys Asp Asp Asp Lys
1               5
```

SNAP-25 REPORTER CONSTRUCTS AND METHODS OF USING THE SAME

CROSS-REFERENCE STATEMENT

This application claims priority under 35 U.S.C. § 119(e) to U.S. Provisional Application 63/033,007 filed Jun. 1, 2020, and the entire content of this provisional application is incorporated herein by reference.

SEQUENCE LISTING

The instant application contains a Sequence Listing which has been submitted electronically in ASCII format and is hereby incorporated by reference in its entirety. Said ASCII copy, created on Aug. 9, 2021, is named 105153-5061_SL.txt and is 15,390 bytes in size.

FIELD OF INVENTION

The present disclosure relates generally to peptide reporter constructs of SNAP-25, which are useful in determining the activity of botulinum toxins.

BACKGROUND

The following discussion is merely provided to aid the reader in understanding the disclosure and is not admitted to describe or constitute prior art thereto.

Botulinum toxin (i.e., botulinum neurotoxin or "BoNT") is a neurotoxic protein produced by the bacterium Clostridium botulinum and related species. BoNT prevents the release of the neurotransmitter acetylcholine from axon endings at the neuromuscular junction and thus causes flaccid paralysis. There are seven main types of botulinum toxin, named type A-G. Botulinum toxins have found numerous commercial uses ranging from the treatment of migraines, hyperactive nerves, excessive sweating, neuropathic pain, chronic pain, muscle disorders (e.g., spasticity and strabismus), and cosmetic applications like treating wrinkles, among other diseases and conditions. BoNTs that are commercially available as pharmaceutical compositions include, for example, BoNT/A preparations like BOTOX® (Allergan, Inc., Irvine, Calif), DYSPORT®/RELOXIN®, (Ipsen Ltd., Slough, England), PURTOX® (Mentor Corp., Santa Barbara, Calif), XEOMIN® (Merz Pharmaceuticals, GmbH., Frankfurt, Germany), NEURONOX® (Medy-Tox, Inc., Ochang-myeon, South Korea), BTX-A (Biogen-tech Ltd., University, Yantai, Shandong, China), AZZALURE® (Galderma, Lausanne, Switzerland); and BoNT/B preparations like MYOBLOC®/NEUROBLOC® (Solstice Neurosciences, Inc., South San Francisco, Calif.). Indeed, the commercial value of botulinum toxin is indisputable.

However, because BoNTs are potent neurotoxins, achieving consistent batch-to-batch consistency in potency is crucial. At present the mouse $LD_{50}$ bioassay, a lethality test, remains the "gold standard" used by all pharmaceutical manufacturers to express the potency of their preparations. In fact, the units on the pharmaceutical preparations' labels are mouse $LD_{50}$ units and the number of animals needed to produce statistically useful $LD_{50}$ data is large. Moreover, the mouse $LD_{50}$ bioassay suffers from many drawbacks including high operational cost due to the large numbers of laboratory animals required, a lack of specificity since all BoNT serotypes will cause the same measurable end-point, and the potential for inaccuracy unless large animal groups are used. In addition, animal rights groups have exerted pressure on regulatory agencies in the U.S. (FDA/NICEATM/ICCVAM) and Europe (MHRA and EDQM) and on pharmaceutical companies manufacturing botulinum neurotoxin products to reduce animal testing and more importantly replace the mouse $LD_{50}$ bioassay for product release.

Accordingly, there is a need in the art for a validated, reproducible method for determining the batch potency of BoNT preparations in order to avoid the continued use of animal-based assays. The present disclosure fulfills that need.

SUMMARY

Described herein are novel SNAP-25 reporter constructs that comprise various combinations of tags or domains to allow for the quantification of BoNT activity in an in vitro assay. Additionally described herein are methods of using the disclosed SNAP-25 reporter constructs to determine and/or quantify BoNT potency and/or activity.

In one aspect, the disclosure provides a peptide reporter comprising a SNAP-25 domain and at least two additional domains selected from a MYC domain, a FLAG domain, and a DIABLO domain.

In some embodiments, one of the at least two additional domains is a MYC domain.

In some embodiments, the SNAP-25 domain comprises SEQ ID NO: 1 or SEQ ID NO: 2.

In some embodiments, the MYC domain comprises SEQ ID NO: 3.

In some embodiments, one of the at least two additional domains is a FLAG domain. In some embodiments, the FLAG domain comprises SEQ ID NO: 4 or SEQ ID NO: 5.

In some embodiments, one of the at least two additional domains is a DIABLO domain. In some embodiments, the DIABLO domain comprises any one of SEQ ID NOs: 7, 8, or 14.

In some embodiments, the peptide comprises: (i) a MYC domain, a -206 domain, and a FLAG domain; (ii) a MYC domain, a -206 domain, a DIABLO domain, and a FLAG domain; (iii) a MYC domain, a DIABLO domain, and a FLAG domain; (iv) a MYC domain, a -206 domain, and a DIABLO domain; (v) MYC domain and a DIABLO domain; or (vi) a MYC domain and a FLAG domain.

In some embodiments, the peptide comprises any one of SEQ ID NOs: 9, 10, 11, 12, or 13. In some embodiments, the peptide comprises amino acids 2-224 of SEQ ID NO: 9; amino acids 2-231 of SEQ ID NO: 10; amino acids 2-222 of SEQ ID NO: 11; amino acids 2-224 of SEQ ID NO: 12; or amino acids 2-215 of SEQ ID NO: 13.

In some embodiments, the SNAP-25 domain can be cleaved by BoNT/A, BoNT/B, BoNT/C, BoNT/D, BoNT/E, BoNT/F, or BoNT/G. In some embodiments, the SNAP-25 domain can be cleaved by BoNT/A, BoNT/C, or BoNT/E.

Also provided herein are methods of determining the enzymatic activity of a sample containing a botulinum neurotoxin (BoNT) comprising, contacting the sample containing a BoNT with the peptide of any one of the foregoing aspects or embodiments and determining whether the peptide was cleaved.

In some embodiments of the disclosed methods, determining whether the peptide was cleaved is established by contacting the peptide with a substrate comprising a capture antibody that specifically binds to one of the at least two additional domains, contacting the bound peptide with a second labeled antibody that specifically binds to a different domain than the capture antibody, washing the bound antibody to remove any unbound labeled antibody, and detecting the signal, if any, of the labeled antibody.

In some embodiments of the disclosed methods, determining whether the peptide was cleaved comprises utilizing an ELISA assay or flow cytometry.

In some embodiments of the disclosed methods, determining whether the peptide was cleaved is established by contacting a cell culture with the peptide and assessing whether the peptide induces apoptosis.

In some embodiments of the disclosed methods, the cell culture is in direct contact with the peptide and the BoNT. In some embodiments of the disclosed methods, the peptide is introduced to the cell culture without the BoNT, but after a period of incubation with the BoNT.

In some embodiments of the disclosed methods, apoptosis is assessed by detecting or assessing at least one of caspase 3/7, caspase 8, caspase 9, DNA fragmentation, phosphatidylserine exposure, TUNEL staining, Annexin V staining, trypan blue permeability, lactate dehydrogenase, or a colorometric tetrazolium salt.

Also provided herein are methods of assessing or quantifying *botulinum* neurotoxin (BoNT) activity comprising contacting a sample containing a BoNT with a SNAP-25 reporter construct comprising (i) a SNAP-25 domain and (ii) at least two additional domains that allow for detection, and determining whether the SNAP-25 reporter construct is cleaved by detecting the presence or absence of the at least two additional domains of the SNAP-25 reporter construct.

In some embodiments of the disclosed methods, determining whether the SNAP-25 reporter construct is cleaved comprises using an ELISA assay or flow cytometry.

In some embodiments of the disclosed methods, the at least two additional domains are selected from the group consisting of a MYC domain, a FLAG domain, a fluorophore, a His tag, an HA tag, a V5 tag, a GFP domain, a GST domain, a β-GAL domain, a luciferase domain, a MBP domain, a RFP domain, a CAT domain, a biotin ligase epitope tag, and a VSV-G domain.

Also provided herein are methods of assessing or quantifying *botulinum* neurotoxin (BoNT) activity comprising contacting a sample containing a BoNT with a SNAP-25 reporter construct comprising (i) a SNAP-25 domain and (ii) at least two additional domains that allow for detection, and determining whether the SNAP-25 reporter construct is cleaved by assessing apoptosis in a cell culture that is contacted with the SNAP-25 reporter either after or during the reporter's contact with the BoNT.

In some embodiments of the disclosed methods, determining whether the SNAP-25 reporter construct is cleaved comprises using an apoptosis assay selected from the group consisting of a colorometric assay utilizing a tetrazolium salt, Annexin V and/or PI staining, a caspase activation assays, a phosphatidylserine localization assay, TUNEL staining, a lactate dehydrogenase localization assay, and trypan blue staining.

In some embodiments of the disclosed methods, one of the at least two additional domains is a DIABLO domain and the second of the at least two additional domains is selected from the group consisting of a MYC domain, a FLAG domain, a fluorophore, a His tag, an HA tag, a V5 tag, a GFP domain, a GST domain, a β-GAL domain, a luciferase domain, a MBP domain, a RFP domain, a CAT domain, a biotin ligase epitope tag, and a VSV-G domain.

Also provided herein are kits comprising a peptide according to any one of the foregoing aspects or embodiments.

In some embodiments, the disclosed kits further comprising a capture antibody bound to a substrate and a detectably labeled antibody.

In some embodiments of the disclosed kits, the capture antibody binds to the MYC domain and the detectably labeled antibody binds to the FLAG domain. In some embodiments of the disclosed kits, the capture antibody binds to the FLAG domain and the detectably labeled antibody binds to the MYC domain.

In some embodiments of the disclosed kits, the substrate is a plate, a slide, or a bead. The kit of claim 26 further comprising at least one apoptosis detection reagent selected from the group consisting of an anti-caspase 3 antibody, an anti-caspase 7 antibody, an anti-caspase 8 antibody, an anti-caspase 9 antibody, Annexin V, trypan blue, and a tetrazolium salt.

Also provided herein are nucleic acids encoding a peptide according to any one of the foregoing aspects or embodiments, as well as expression vectors comprising such nucleic acids and cells comprising such nucleic acids or the expression vectors. In some embodiments, the cell is a mammalian cell, such as a human embryonic kidney cell (HEK).

The foregoing general description and following detailed description are exemplary and explanatory and are intended to provide further explanation of the disclosure as claimed. Other objects, advantages, and novel features will be readily apparent to those skilled in the art from the following brief description of the drawings and detailed description of the disclosure.

BRIEF DESCRIPTION OF THE DRAWINGS

FIG. 1 shows the sequences of the disclosed SNAP-25 reporter constructs. (A) shows a SNAP-25 reporter comprising a human SNAP-25 domain, a MYC tag at the N-terminus of the SNAP-25 domain, and a −206 sequence and a FLAG tag at the C-terminus of the SNAP-25 domain (SEQ ID NO: 9). (B) shows a SNAP-25 reporter comprising a human SNAP-25 domain, a MYC tag at the N-terminus of the SNAP-25 domain, and a −206 sequence, a DIABLO sequences, and a FLAG tag at the C-terminus of the SNAP-25 domain (SEQ ID NO: 10). (C) shows a SNAP-25 reporter comprising a human SNAP-25 domain, a MYC tag at the N-terminus of the SNAP-25 domain, and a DIABLO sequence and a FLAG tag at the C-terminus of the SNAP-25 domain (SEQ ID NO: 11). (D) shows a SNAP-25 reporter comprising a human SNAP-25 domain, a MYC tag at the N-terminus of the SNAP-25 domain, and a −206 sequence and a DIABLO sequence at the C-terminus of the SNAP-25 domain (SEQ ID NO: 12). (E) shows a SNAP-25 reporter comprising a human SNAP-25 domain, a MYC tag at the N-terminus of the SNAP-25 domain, and a DIABLO sequence at the C-terminus of the SNAP-25 domain (SEQ ID NO: 13).

FIG. 7 shows an exemplary Western blot used to quantify the ration of cleaved and uncleaved SNAP-25 in the potency assay. The primary antibody was an anti-c-MYC antibody against the MYC tag in Reporter1 protein.

FIG. 8 shows dose-response [log(agonist) vs. response-non-linear regression] curves indicating SNAP-25 cleavage. Panel A shows cleavage detected in samples incubated for 4 hours at ambient temperature $R^2=0.9998$, EC50=843.9. Panel B shows percentage of cleavage calculated based on Western blot (WB) analysis of reaction samples incubated for 22 hours at room temperature $R^2=0.9939$ EC50=204.5. Panel C shows SNAP-25 cleavage percentage estimated in samples incubated for 22 hours at 37° C. $R^2=0.9409$ EC50=687.4. Y axis values were adjusted according to the highest percentage of cleavage measured in every group of samples.

DETAILED DESCRIPTION

Figure 2:
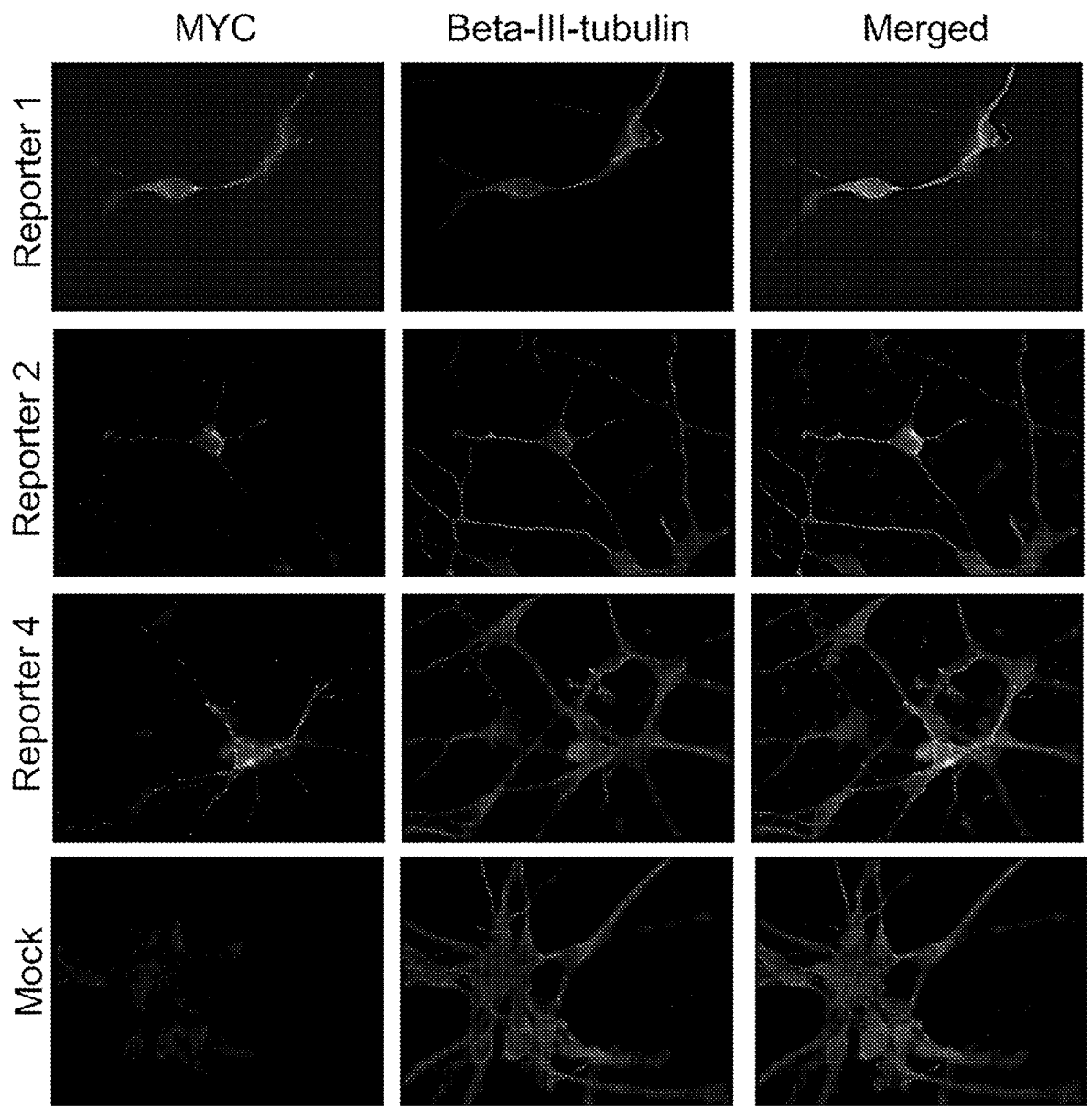
FIG. 2 shows that the disclosed SNAP-25 reporters can be expressed in human neurons derived from pluripotent stem cells. These neurons are GABAnergic.
Figure 3:
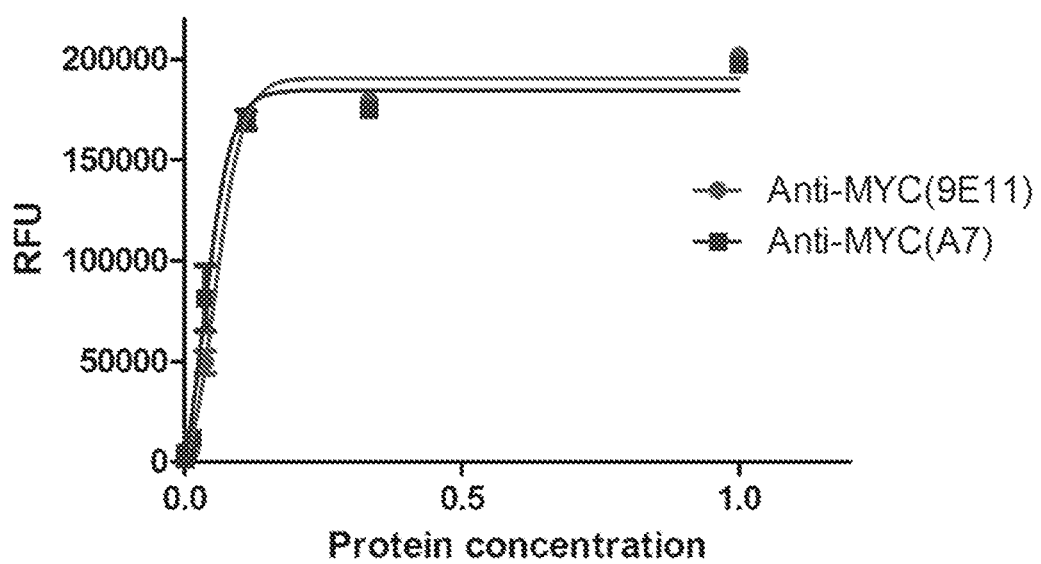
FIG. 3 shows that the cleavage of SNAP-25 reporter 1 can be detected using enzyme-linked immunosorbent assay (ELISA) with antibodies directed towards the Myc and FLAG affinity tags.

The present disclosure provides SNAP-25 reporter constructs that comprise various combinations of tags (e.g., MYC or FLAG) or domains (e.g., DIABLO) to allow for the quantification of BoNT activity in an in vitro assay. These novel SNAP-25 reporter constructs and the methods disclosed herein provide a needed alternative to the traditional animal testing models used for determining activity of BoNTs.

I. Definitions

It is to be understood that methods are not limited to the particular embodiments described, and as such may vary. It is also to be understood that the terminology used herein is for the purpose of describing particular embodiments only, and is not intended to be limiting. The scope of the present technology will be limited only by the appended claims.

As used herein, certain terms may have the following defined meanings. As used in the specification and claims, the singular form "a," "an" and "the" include singular and plural references unless the context clearly dictates otherwise. For example, the term "a peptide" includes a single peptide as well as a plurality of peptides, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "about" means plus or minus 10% as well as the specified number. For example, "about 10" should be understood as both "10" and "9-11."

As used herein, "optional" or "optionally" means that the subsequently described event or circumstance may or may not occur, and that the description includes instances where said event or circumstance occurs and instances where it does not.

The term "SNAP-25 domain" as used herein refers to a peptide sequence or fragment thereof of a human SNAP-25 protein (Entrez 6616; UniProt P60880). In some embodiments, the SNAP-25 domain may comprise the amino acid sequence MAEDADMRNELEEMQRRADQLADE SLESTRRMLQLVEESKDAGIRTLVMLDEQGEQL ERIEEGMDQINKDMKEAEKNLTDLGKFCGL CVCPCNKLKSSDAYKKAWGNNQDGVVA SQPARVVDEREQMAISGGFIRRVTNDARENEMDENLEQVSGIIGNLRHMALDMGNEIDT QNRQIDRIMEKADSNKTRIDEANQ (SEQ ID NO: 1). In some embodiments, the SNAP-25 domain may comprise the amino acid sequence MAEDADMRNELEEMQRRADQLADESLESTRRMLQLVEESKDAGIRTLVMLDEQGEQL ERIEEGMDQINKDMKEAEKNLTDLG KFCGLCVCPCNKLKSSDAYKKAWGNNQDGVVA SQPARVVDEREQMAISGGFIRRVTNDARENEMDENLEQVSGIIGNLRHMALDMGNEIDT QNRQIDRIMEKADSNKTRIDEANQRATKMLGSG (SEQ ID NO: 2). In some embodiments, the SNAP-25 domain may not comprise the N-terminal methionine of SEQ ID NO: 1 or SEQ ID NO: 2.

The terms "MYC domain" or "MYC tag" as used herein refer to a peptide sequence or fragment thereof of a Myc family transcription factor, which can include c-Myc (NCBI gene 4609; RefSeq NM_001354870.1; UniProt P01106), 1-Myc (NCBI gene 4610; RefSeq NM_005376; UniProt P12524), and n-Myc (NCBI gene 4613, RefSeq NM_005378, UniProt P04198). In some embodiments, the MYC domain may comprise the amino acid sequence EQKLISEEDL (SEQ ID NO: 3).

The terms "FLAG domain" or "FLAG tag" as used herein refer to a polypeptide tag that can be used in a variety of different assays to identify the tagged protein. FLAG domain sequences can comprise the amino acid sequence DYKDDDK (SEQ ID NO: 4) or DYKDDDDK (SEQ ID NO: 5).

The term "−206 domain" as used herein refers to a sequence that represents the last 9 amino acids at the C-terminus of a SNAP-25 peptide (i.e., amino acid residues 198-206 of NCBI Ref Sequences NP_001309831, NP_001309832, NP_001309833, NP_001309834, or NP_001309835). In some embodiments, the −206 domain may comprise the amino acid sequence RATKMLGSG (SEQ ID NO: 6).

The term "DIABLO domain" as used herein refers to a peptide sequence or fragment thereof of a mitochondrial protein (Entrez 56616; UniProt Q9NR28) encoded by the DIABLO gene (also known as mitochondria-derived activator of caspases (SMAC)). This protein binds inhibitor of apoptosis proteins (IAPB), thus freeing caspases to activate apoptosis. In some embodiments, the DIABLO domain may comprise the amino acid sequence AVPIAQK (SEQ ID NO: 7) or QAVPIAQ (SEQ ID NO: 8). In some embodiments, the DIABLO domain comprises at least the minimum active portion of the peptide conferring apoptosis signaling: AVPI (SEQ ID NO: 14).

II. SNAP-25 Reporter Constructs

Synaptosomal nerve-associated protein 25 (SNAP-25) is a t-SNARE protein that is encoded by the SNAP25 gene in humans. SNAP-25 is anchored to the cytosolic face of membranes via palmitoyl side chains covalently bound to cysteine amino acid residues in the middle of the molecule, and it does not contain a trans-membrane domain. SNAP-25 exists in two different isoforms (SNAP-25A and SNAP-25B), and the full-length wild-type protein sequence is 206 amino acids long (see NCBI Ref Sequences NP_001309831, NP_001309832, NP_001309833, NP_001309834, NP_001309835). SNAP-25 is a natural substrate of *botulinum* toxins, and it is cleaved by *botulinum* toxins BoNT/A, BoNT/C, and BoNT/E.

The presently disclosed SNAP-25 reporter complexes comprise a SNAP-25 domain connected to various peptide tags (e.g., MYC or FLAG) or domains (e.g., DIABLO) to allow for the quantification of BoNT activity in an in vitro assay. In some embodiments, the SNAP-25 domain of the reporter construct may be a fragment of the SNAP-25 protein comprising 170, 175, 180, 185, 190, 191, 192, 193, 194, 195, 196, 197, 198, 199, 200, 201, 202, 203, 204, 205, or 206 amino acids. In some embodiments, the SNAP-25 domain of the reporter construct may comprise the amino acid sequence of SEQ ID NO: 1. In some embodiments, the SNAP-25 domain of the reporter construct my comprise the amino acid sequence of SEQ ID NO: 2.

In some embodiments, a SNAP-25 domain may possess about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% amino acid sequence homology to SEQ ID NO: 1 or SEQ ID NO: 2. Indeed, for the purposes of the disclosed SNAP-25 reporter constructs, any of the foregoing SNAP-25 homologs can be suitably incorporated into the construct so long as it is able to be cleaved by commercially available BoNTs, including but not limited to, BOCOUTURE®, AZZALURE®, QM1114, DYSPORT®, XEOMIN®, and BOTOX®, as well as any other BoNT/A, BoNT/B, BoNT/C, BoNT/D, BoNT/E, BoNT/F, or BoNT/G. In some embodiment, any of the foregoing SNAP-25 homologs can be suitably incorporated into the construct so long as it is able to be cleaved by BoNT/A, BoNT/C, or BoNT/E.

The disclosed SNAP-25 reporters additionally comprise at least two tags or domains that allow for detection. In some embodiments, the tags/domains may include a MYC domain, a FLAG domain, and/or a DIABLO domain. In some embodiments, however, other tags or recognition domains may be utilized in the SNAP-25 reporter in addition to or in the alternative to a MYC domain, a FLAG domain, and/or a DIABLO domain. For example, in some embodiments two tags or domains that allow for detection can include, but are not limited to, a fluorophore or fluorescent tag, a His tag (a repeat of histidine residues usually comprising at least about 3, 4, 5, 6, or 7 of more histidines), an hemagglutinin (HA) tag, a V5 tag, a GFP (green fluorescent protein) domain, a GST (glutathione-S-transferase) domain, a β-GAL (β-galactosidase) domain, a luciferase domain, a MBP (Maltose Binding Protein) domain, a RFP (Red Fluorescence Protein) domain, a CAT (Chloramphenicol-Acetyl Transferase) domain, a biotin ligase epitope tag, and/or a VSV-G (Vesicular Stomatitis Virus Glycoprotein) domain.

In some embodiments, the SNAP-25 reporter may comprise, in addition to the SNAP-25 domain, (i) a MYC domain, a −206 domain, and a FLAG domain; (ii) a MYC domain, a −206 domain, a DIABLO domain, and a FLAG domain; (iii) a MYC domain, a DIABLO domain, and a FLAG domain; (iv) a MYC domain, a −206 domain, and a DIABLO domain; (v) MYC domain and a DIABLO domain; or (vi) a MYC domain and a FLAG domain.

For the purposes of the disclosed SNAP-25 reporter constructs, the MYC domain may comprise a portion or fragment of a Myc family transcription factor, such as c-Myc, l-Myc, or n-Myc. The fragment of the Myc family transcription factor may be 5, 6, 7, 8, 9, 10, 11, 12, 13, 14, or 15 or more amino acids in length. In some embodiments, the MYC domain may comprise SEQ ID NO: 3.

For the purposes of the disclosed SNAP-25 reporter constructs, the FLAG domain may comprise a portion or fragment of a FLAG tag peptide. The FLAG domain may be 5, 6, 7, 8, 9, 10, 11, 12, 13, 14, or 15 or more amino acids in length. In some embodiments, the FLAG domain may comprise SEQ ID NO: 4 or SEQ ID NO: 5.

For the purposes of the disclosed SNAP-25 reporter constructs, the DIABLO domain may comprise a portion or fragment of a mitochondrial DIABLO protein, also known as second mitochondria-derived activator of caspases or SMAC. The fragment of the DIABLO protein may be 5, 6, 7, 8, 9, 10, 11, 12, 13, 14, or 15 or more amino acids in length. In some embodiments, the DIABLO domain may comprise any one of SEQ ID NO: 7 or SEQ ID NO: 8.

Five exemplary SNAP-25 reporter constructs are disclosed in FIG. 1 and in Table 1 below.

TABLE 1

| Reporter Name | SEQ ID NO: | Amino Acid Sequence |
|---|---|---|
| SNAP-25 Reporter 1 | 9 | MEQKLISEEDLMAEDADMRNELEEMQRRADQLADE SLESTRRMLQLVEESKDAGIRTLVMLDEQGEQLERIE EGMDQINKDMKEAEKNLTDLGKFCGLCVCPCNKLK SSDAYKKAWGNNQDGVVASQPARVVDEREQMAISG GFIRRVTNDARENEMDENLEQVSGIIGNLRHMALDM GNEIDTQNRQIDRIMEKADSNKTRIDEANQRATKML GSKDYKDDDK |

TABLE 1-continued

| Reporter Name | SEQ ID NO: | Amino Acid Sequence |
|---|---|---|
| SNAP-25 Reporter 2 | 10 | MEQKLISEEDLMAEDADMRNELEEMQRRADQLADE SLESTRRMLQLVEESKDAGIRTLVMLDEQGEQLERIE EGMDQINKDMKEAEKNLTDLGKFCGLCVCPCNKLK SSDAYKKAWGNNQDGVVASQPARVVDEREQMAISG GFIRRVTNDARENEMDENLEQVSGIIGNLRHMALDM GNEIDTQNRQIDRIMEKADSNKTRIDEANQRATKML GSGAVPIAQKDYKDDDK |
| SNAP-25 Reporter 3 | 11 | MEQKLISEEDLMAEDADMRNELEEMQRRADQLADE SLESTRRMLQLVEESKDAGIRTLVMLDEQGEQLERIE EGMDQINKDMKEAEKNLTDLGKFCGLCVCPCNKLK SSDAYKKAWGNNQDGVVASQPARVVDEREQMAISG GFIRRVTNDARENEMDENLEQVSGIIGNLRHMALDM GNEIDTQNRQIDRIMEKADSNKTRIDEANQAVPIAQK DYKDDDK |
| SNAP-25 Reporter 4 | 12 | MEQKLISEEDLMAEDADMRNELEEMQRRADQLADE SLESTRRMLQLVEESKDAGIRTLVMLDEQGEQLERIE EGMDQINKDMKEAEKNLTDLGKFCGLCVCPCNKLK SSDAYKKAWGNNQDGVVASQPARVVDEREQMAISG GFIRRVTNDARENEMDENLEQVSGIIGNLRHMALDM GNEIDTQNRQIDRIMEKADSNKTRIDEANQRATKML GSGAVPIAQK |
| SNAP-25 Reporter 5 | 13 | MEQKLISEEDLMAEDADMRNELEEMQRRADQLADE SLESTRRMLQLVEESKDAGIRTLVMLDEQGEQLERIE EGMDQINKDMKEAEKNLTDLGKFCGLCVCPCNKLK SSDAYKKAWGNNQDGVVASQPARVVDEREQMAISG GFIRRVTNDARENEMDENLEQVSGIIGNLRHMALDM GNEIDTQNRQIDRIMEKADSNKTRIDEANQAVPIAQK |

In some embodiments, a SNAP-25 reporter construct may possess about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% amino acid sequence homology to any of the peptide sequences disclosed in Table 1.

In some embodiments, the disclosed SNAP-25 report constructs may comprise an amino acid sequence of any one of SEQ ID NOs: 9, 10, 11, 12, or 13. In some embodiments, a SNAP-25 reporter may comprise amino acids 2-224 of SEQ ID NO: 9 (i.e., the entire SEQ ID NO: 9 sequences minus the N-terminal methionine). In some embodiments, a SNAP-25 reporter may comprise amino acids 2-231 of SEQ ID NO: 10 (i.e., the entire SEQ ID NO: 10 sequences minus the N-terminal methionine). In some embodiments, a SNAP-25 reporter may comprise amino acids 2-222 of SEQ ID NO: 11 (i.e., the entire SEQ ID NO: 11 sequences minus the N-terminal methionine). In some embodiments, a SNAP-25 reporter may comprise amino acids 2-224 of SEQ ID NO: 12 (i.e., the entire SEQ ID NO: 12 sequences minus the N-terminal methionine). In some embodiments, a SNAP-25 reporter may comprise amino acids 2-215 of SEQ ID NO: 13 (i.e., the entire SEQ ID NO: 13 sequences minus the N-terminal methionine).

The disclosed SNAP-25 reporter constructs may be cleaved by any number of commercially available BoNTs, including but not limited to, BOCOUTURE®, AZZALURE®, QM1114, DYSPORT®, XEOMIN®, and BOTOX®, as well as other BoNT/A, BoNT/B, BoNT/C, BoNT/D, BoNT/E, BoNT/F, or BoNT/G.

Also provided herein are nucleic acids encoding the disclosed SNAP-25 reporter constructs. In some embodiments, the nucleic acid encodes a peptide sequence comprising a SNAP-25 domain and two or more tags/domains that allow for in vitro detection such as, for example, (i) a MYC domain, a −206 domain, and a FLAG domain; (ii) a MYC domain, a −206 domain, a DIABLO domain, and a FLAG domain; (iii) a MYC domain, a DIABLO domain, and a FLAG domain; (iv) a MYC domain, a −206 domain, and a DIABLO domain; (v) MYC domain and a DIABLO domain; or (vi) a MYC domain and a FLAG domain. In some embodiments, the nucleic acid encodes a peptide comprising any one of SEQ ID NOs: 11, 12, 13, 14, or 15, or a peptide comprising about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% amino acid sequence homology thereto. The disclosed nucleic acid sequences may be incorporated into an expression vector so that the encoded protein/peptide can be expressed in any suitable expression system (e.g., *E. coli* or other bacterial expression systems, yeast expression systems, insect expression systems such as Sf9 or Sf21, mammalian expression systems such as Chinese hamster ovary (CHO) cells or human embryonic kidney (HEK) cells, fibroblasts, stem cells, etc.).

III. Methods of Using SNAP-25 Reporter Constructs

The disclosed SNAP-25 reporters are useful for a variety of clinical and commercial applications for determining *botulinum* toxin activity.

Depending on the tags or reporter domains, the disclosed SNAP-25 report constructs may be incorporated into a variety of assay formats for tracking activity. For the purposed of the disclosed methods, a SNAP-25 reporter comprises (i) a SNAP-25 domain that may possess about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% amino acid sequence homology to SEQ ID NO: 1 or SEQ ID NO: 2 or a fragment thereof so long as the homolog or fragment may be cleaved by a BoNT, and (ii) at least two tags or domains that allow for detection. In some embodiments, the tags/domains may include a MYC domain, a FLAG domain, and/or a DIABLO domain. In some embodiments, however, other tags or recognition domains may be utilized in the SNAP-25 reporter in addition to or in the alternative to a MYC domain, a FLAG domain, and/or a DIABLO domain. For example, in some embodiments, the at least two tags or domains that allow for detection can include, but are not limited to, a MYC domain, a FLAG domain, a DIABLO domain, a His tag (a repeat of histidine residues usually comprising at least about 3, 4, 5, 6, or 7 of more histidines), an hemagglutinin (HA) tag, a V5 tag, a GFP (green fluorescent protein) domain, a GST (glutathione-S-transferase) domain, a β-GAL (β-galactosidase) domain, a luciferase domain, a MBP (Maltose Binding Protein) domain, a RFP (Red Fluorescence Protein) domain, a CAT (Chloramphenicol-Acetyl Transferase) domain, a biotin ligase epitope tag, and/or a VSV-G (Vesicular Stomatitis Virus Glycoprotein) domain.

In some embodiments (e.g., SNAP-25 reporter 1 or SEQ ID NO: 9), reporters tagged with a MYC domain and a FLAG domain will have a loss of signal when the reporter is cleaved by a BoNT, and this will allow detection and quantification of BoNT activity in that context of, for example, an ELISA assay, flow cytometry, Western blot, surface plasmon resonance, liquid chromatography-mass spectroscopy (LC-MS), protein ligation assay (PLA), or other similar format. In this type of embodiment, the uncleaved reporter would be recognized by reagents that bind to both the MYC domain and the FLAG domain, but once the reporter is cleaved, the recognition domains (i.e., MYC and FLAG are separated). As a result, one of the two signals is lost. In the context of an ELISA, for example, a capture antibody against one of the two tags can be attached to a substrate (e.g., a plate, slide, or bead) and the substrate comprising the capture antibodies can be contacted with the reporter and, subsequently, a labeled antibody that binds to the other tag (i.e., the tag not recognized by the capture antibody). Labeled antibodies can be "labeled" with any known detection reagent including, but not limited to, a fluorophore, an enzyme (horseradish peroxidase), a gold particle, a magnetic particle, a radiolabel/isotope, or any other detectable label. In this format, the presence of the signal of the labeled antibody would indicate a lack of cleavage of the reporter, whereas the absence of the signal would indicate cleavage of the reporter.

Thus, in some embodiments, the present disclosure provides methods of assessing and/or quantifying BoNT activity comprising contacting a sample containing a BoNT with a SNAP-25 reporter construct as disclosed herein and directly determining whether the SNAP-25 reporter construct is cleaved by detecting the presence or absence of at least one of the tags or domains of the SNAP-25 reporter construct. In some embodiments, the detection can be performed using an ELISA assay, flow cytometry, or other similar assay formats.

In some embodiments (e.g., SNAP-25 reporters 2-5 or SEQ ID NOs: 10-13) reporters tagged with DIABLO (or another apoptotic/apoptosis signaling peptide) will produce an apoptotic peptide when the reporter is cleaved by a BoNT, and therefore can be incorporated into any number of apoptosis assay formats (e.g., colorometric assays utilizing tetrazolium salts like MTT, XTT, or WST; Annexin V and/or PI staining; caspase activation assays such as those that detect caspase 3/7, caspase 8, or caspase 9; phosphatidylserine localization assays; TUNEL staining; lactate dehydrogenase localization; trypan blue staining; etc.). In this type of embodiment, the reporter can be incubated with a BoNT to induce cleavage of the reporter. In some embodiments, this incubation of the reporter with a BoNT can be completed in the presence of cultured cells (e.g., an HEK cells) and the amount and rate of apoptosis can be measured directly from the cell culture. Alternatively, in some embodiments, the incubation of the reporter with a BoNT can be completed in isolation (i.e., without cells being present), and the incubation product can be introduced to a cell culture at various times to assess whether apoptosis-inducing reporter products are being produced by the incubation of the reporter and the BoNT. Other suitable apoptosis assays include, but are not limited to the APOTOX-GLO™ Triplex Assay (Promega), CellEvent Caspase-3/7 Flow cytometry assay kit (#C10740 from ThermoFisher), and Cytockrome C apoptosis ICC assay kit (#Ab110417 Abcam). For method that utilize flow cytometry, suitable assays and kits include, but are not limited to, Vybrant FAM Poly Caspases Assay kit (#35117, ThermoFisher) and Annexin V/ANXAS-FITC Apoptosis Detection Reagents (#ab14082 Abcam). Suitable imaging assays include, but are not limited to, CellEvent Caspases-3/7 Green detection (#C10723 ThermoFisher), apoptosis/necrosis assay kit #ab176749 from Abcam.

Thus, in some embodiments, the present disclosure provides methods of assessing and/or quantifying BoNT activity comprising contacting a sample containing a BoNT with a SNAP-25 reporter construct as disclosed herein and indirectly determining whether the SNAP-25 reporter construct is cleaved by assessing apoptosis in a cell culture that is contacted with the SNAP-25 reporter either after or during the reporter's contact with the BoNT. In some embodiments, the detection can be performed using any known apoptosis assay format including, but not limited to, colorometric assays utilizing tetrazolium salts like MTT, XTT, or WST; Annexin V and/or PI staining; caspase activation assays such as those that detect activity of caspase 3/7, caspase 8, or caspase 9; phosphatidylserine localization assays; TUNEL staining; lactate dehydrogenase localization; or trypan blue staining.

The present disclosure provides methods of assessing or determining *botulinum* toxin activity in a sample by contacting the sample of *botulinum* toxin with a SNAP-25 reporter construct and assessing or determining whether the SNAP-25 reporter is cleaved. In some embodiments, assessing or determining whether cleavage of the SNAP-25 reporter has occurred may comprise detecting/determining the presence or absence of one or more of the tags or domains on the SNAP-25 reporter. In some embodiments, assessing or determining whether cleavage of the SNAP-25 reporter has occurred may comprise assessing apoptosis in a cell culture that is either in direct contact with the SNAP-25 reporter and BoNT or indirectly contacted by the product of the SNAP-25 reporter and BoNT.

The following examples are given to illustrate the present invention. It should be understood, however, that the invention is not to be limited to the specific conditions or details described in these examples.

EXAMPLES

Example 1—Construction of Modified SNAP-25 Reporters

Five genetically modified versions of SNAP-25 which can be expressed in cell-lines, cells derived from embryonic stem cells, and cells derived from inducible stem cells were designed and validated. The readout from these constructs is based on two principles:

First, some versions include SNAP-25 tagged with Myc and FLAG tags (FIG. 1A, SNAP-25 reporter 1) in the N and C terminus, respectively. These tags are separated when the SNAP-25 reporters are cleaved by a neurotoxin and a loss of signal in response to neurotoxin cleavage can be detected by antibodies against these tags.

Second, some versions include SNAP25 with a minimal diablo (DIABLO or SMAC) peptide (FIG. 1B-E, SNAP-25 reporter 2-5). This peptide is exposed in response to cleavage of the SNAP-25 reporter by neurotoxins and induces cell-death through the apoptosis pathway, which can be detected using various apoptosis detection reagents and system.

Figure 4:
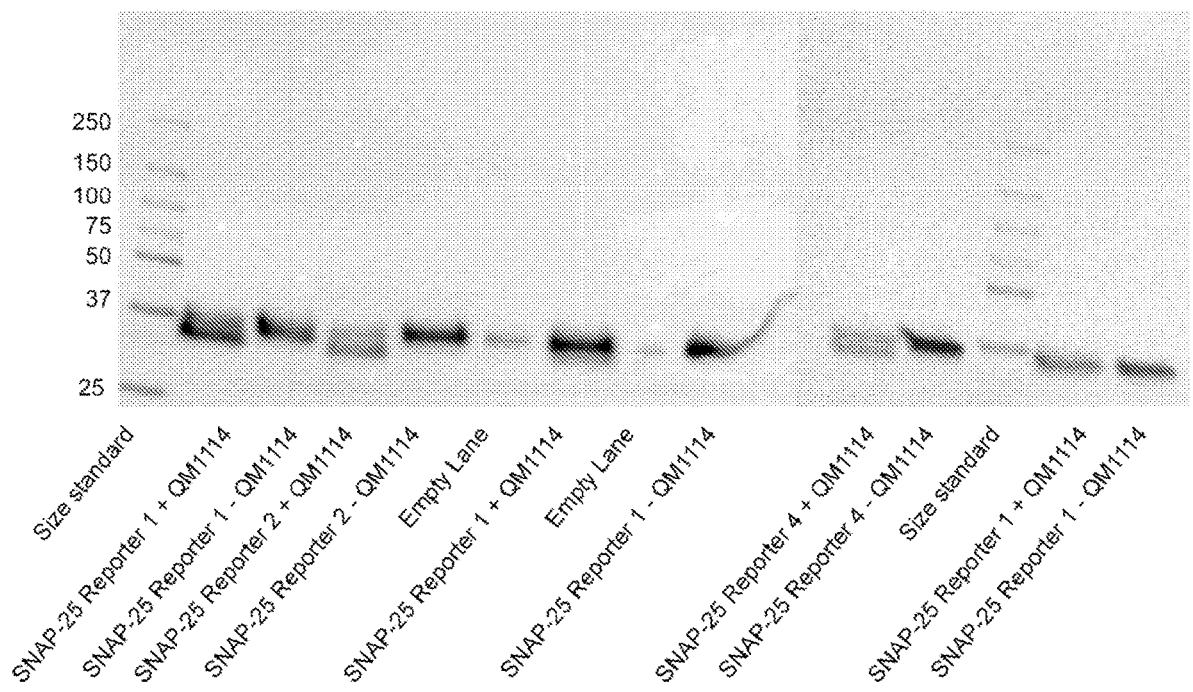
FIG. 4 shows that SNAP-25 reporters 1, 2, and 4 are effectively cleaved by BoNT/A and that SNAP-25 reporters 3 and 5 show intermediate cleavage by BoNT/A.
Figure 5:
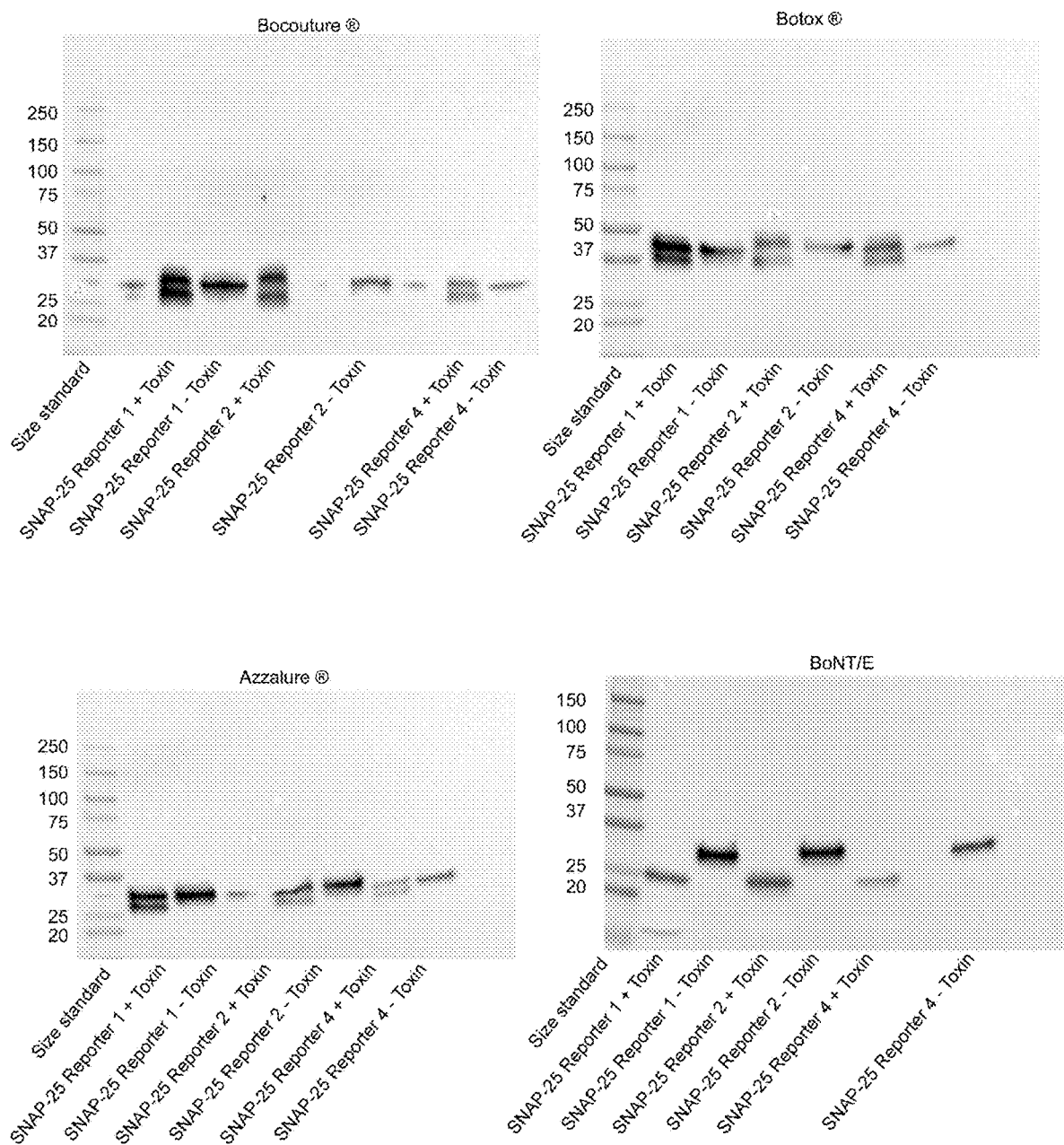
FIG. 5 shows that SNAP-25 reporters 1, 2, and 4 can be cleaved by several commercial BoNT/A products (BOCOUTURE®, AZZALURE®, and BOTOX®) as well as BoNT/E.
Figure 6:
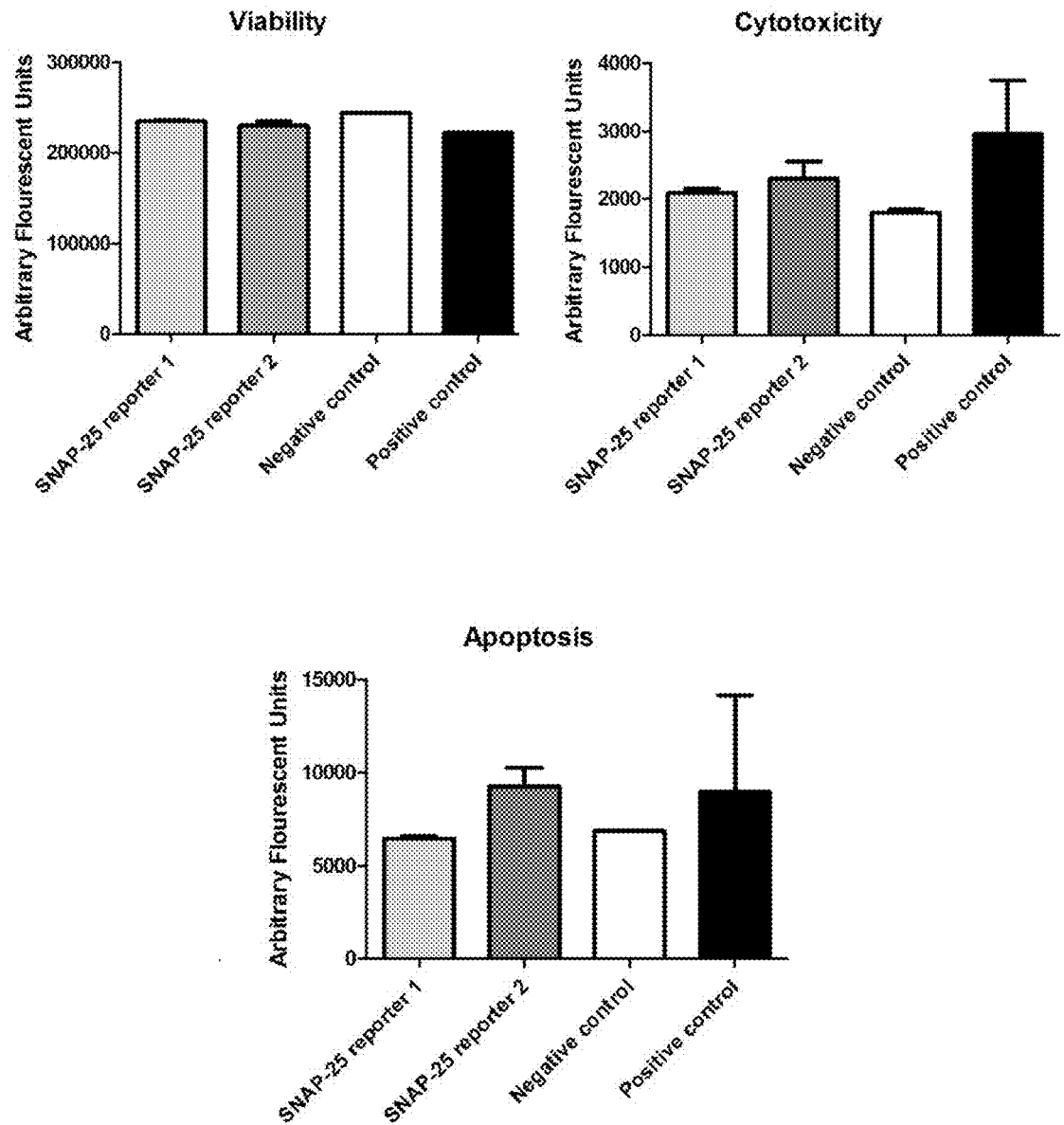
FIG. 6 shows that the peptide resulting from cleavage of SNAP-25 reporters 2 and 4 by BoNT/A and BoNT/E effectively induces apoptosis in cells.

These genetically modified reporters can be used to determine potency of neurotoxins that cleave SNAP-25, such as *botulinum* toxin type A (BoNT/A) and *botulinum* toxin type E (BoNT/E). These reporters can further be used as model systems for a bioassay to determine potency of clinical preparations of BoNT/A and BoNT/E. Regarding these reporter constructs, it has been shown:

- That SNAP-25 reporters 1, 2, and 4 can be expressed in neurons derived from stem cells (FIG. 2) and continuous HEK-293 cells;
- That cleavage of SNAP-25 reporter 1 can be detected using enzyme-linked immunosorbent assay (ELISA) with antibodies directed towards the Myc and FLAG affinity tags (FIG. 3);
- That SNAP-25 reporters 1, 2, and 4 are most effectively cleaved by BoNT/A and that SNAP-25 reporters 3 and 5 show intermediate cleavage by BoNT/A (FIG. 4);
- That SNAP-25 reporters 1, 2, and 4 can be cleaved by several commercial BoNT/A products (such as BOCOUTURE®, AZZALURE®, QM1114, DYSPORT®, XEOMIN®, and BOTOX®) as well as BoNT/E. (FIG. 5); and
- That the peptide resulting from cleavage of SNAP-25 reporters 2 and 4 by BoNT/A and BoNT/E effectively induces apoptosis in cells (FIG. 6).

The five different versions of SNAP-25 were based on human SNAP-25b and were codon optimized for expression in human cells. One expresses a MYC (EQKLISEEDL; SEQ ID NO: 3) and FLAG (KDYKKDDDK; SEQ ID NO: 15) tagged version of SNAP-25 (FIG. 1A), to enable detection of cleaved SNAP-25 using ELISA using tag antibodies. The others are various version of SNAP-25 with DIABLO (SMAC) inserted near the C-termini (FIGS. 1B-1E). The rationale for the latter version of SNAP-25 is that DIABLO will be exposed upon cleavage of the SNAP-25 reporter and induce apoptosis through activation of Caspase 9, which can be detected using Caspase 9 or generally available apoptosis kits, such as CASPASE-GLOR 9 Assay (Promega), CASP-GLOW™ Fluorescein Active Caspase-9 Staining Kit (Invitrogen), or Caspase 9 Colorimetric Activity Assay Kit (Millipore Sigma).

In general, the five SNAP-25 reporters can be described generally as:

- Reporter 1: MYC-tagged N-terminal and FLAG-tagged C-terminal;
- Reporter 2: MYC-tagged N-terminal and FLAG-tagged C-terminal along with a DIABLO segment in the C-terminal;
- Reporter 3: MYC-tagged N-terminal and FLAG-tagged C-terminal along with a DIABLO segment in the C-terminal, amino acid 197-206 in SNAP-25 were removed;
- Reporter 4: MYC-tagged N-terminal and with a DIABLO segment in the C-terminal; and
- Reporter 5: MYC-tagged N-terminal and with a DIABLO segment in the C-terminal, amino acid 197-206 in SNAP-25 were removed.

Example 2—Expression of SNAP-25 Transporters in Human Induced Pluripotent Stem Cells and HEK-293

Human glutamatergic induced pluripotent stem cells (iPSC) from Cellular Dynamics were transfected using pcDNA3.1 plasmids containing SNAP-25 reporters 1, 2, 4, or a negative control (mock). The transfection was performed using Lipofectamine 3000. After 48 h, the cells were washed and fixed using 4% parafolmaldehyde. Immunocytochemistry using antibodies for SNAP-25 (S9684, Sigma) as well as against the MYC and FLAG tags were used to the reveal correct expression and localization of the SNAP-25 reporters with the fluorescent signal accumulation along the membrane and projections of the cells (see FIG. 2). The reporters were well tolerated by the cells and were expressed in the correct sub-cellular localization.

HEK-293 cells were likewise transfected with the same reporter constructs. As with the iPS cells, the reporters were expressed in the plasma membrane of the HEK-293 cells. These expressing cells were further used to purify the constructs for in vitro cleavage by *Botulinum* toxins, clearly showing that these reporters are expressed.

Example 3—Detection of SNAP-25 Reporter 1 using ELISA

Whole protein preparations from HEK-293 cells overexpressing Reporter 1 were used in a sandwich ELISA. Two monoclonal anti-Myc antibodies (clones 9E11 and A7) were used as capture molecules at a dilution of 1:500. A 1:3 serial dilution of the protein samples, starting at 100 μg/ml) were loaded and detected using monoclonal anti-FLAG antibody (Clone M2) directly labeled with HRP. Signal detection was performed using SuperSignal ELISA Pico Chemiluminescence substrate (Thermo Scientific). The relative fluorescent signal compared to the protein's concertation revealed a strong signal with little background noise. This reporter can be expressed in cells and works in a sandwich ELISA with two different anti-Myc antibodies, not requiring any SNAP-25 specific antibody (FIG. 3).

Example 4—Cleavage of SNAP-25 Reporters by BoNT/A and BoNT/E

The constructs were expressed in pcDNA3 vectors that were transiently transfected into HEK-293 cells by transfection with Lipofectamine 3000. Approximately $0.8\times10^6$ cells/well were transfected in 6 well plates and harvested 48 h post transfection. The cells were lysed in RIPA buffer and SNAP-25 was purified on magnetic beads coupled with anti-FLAG antibody (Clone M2, Thermo Fisher). Further, the purified constructs were cleaved using BoNT (QM1114, XEOMIN®, AZZALURE®, BOTOX®, and research grade BoNT/E (List laboratories) at a concentration of 500 units/ml in 100 μl of reaction buffer containing (HEPES 20 μM; NaCl 10 mM; 1% Tween 20; $ZnCl_2$ 100 μM; DTT 5 mM).

Incubation time was 18 h at room temperature and after that 10 µl of the samples were analyzed by Western blot (FIGS. 4 and 5).

Example 5—Induction of Apoptosis by DIABLO (SMAC) Fragments Resulting from BoNT/A and BoNT/E Cleavage of SNAP-25 Reporter 2 and 4

SNAP-25 Reporter 2 and 4 were evaluated in an apoptosis assay to show that these reporters are able to induce apoptosis upon cleavage. Because none of the cells that take up BoNT/A can be transiently transfected with the constructs at high enough efficiency, an indirect method was used. Short peptides representing the fragments downstream of the cleavage site of SNAP-25 Reporter 2 and 4 were designed to mimic the part of the reporter that is released upon BoNT/A cleavage. Previous experiments utilizing Reporter 3 showed that the constructs can be cleaved by BoNT/A, and therefore treating cells with these peptides is sufficient to show that the cleaved constructs can induce apoptosis. Since no toxin intake was necessary for these experiments, HEK-293 were used to investigate the effects of the cleavage product in a cell system. Pierce Protein Transfection Reagent was used to transfect the peptides into HEK-293 cells. Only the peptides representing SNAP-25 Reporter 2 and 4 showed any activation of apoptosis, and only data from these peptides are shown. For instance, FIG. 6 shows that SNAP-25 Reporter 2 and SNAP-25 Reporter 4 induce apoptosis, but induce minimal cytotoxicity (from the transfection) and no reduced total viability. Significantly, SNAP-25 Reporter 2 induces apoptosis to the same degree as the apoptosis inducer used as a positive control.

Example 6—Evaluation of Potency Detection Assay

To evaluate whether the disclosed constructs could be used as a basis for a potency detection assay for BoNT/A, a method was developed. Reporter 1 was expressed in HEK-293 cells and purified on a gravity flow Myc affinity column. Samples were eluted with either 3M NaSCN or 10× c-MYC peptide. NaSCN elution gave highest concentration of Reporter 1 protein and was used for further tests. Briefly the analytical method was based on the following steps:

1. Reduce BoNT/A (here the Galderma BoNT/A drug product QM-1114 at 6000 U/ml was used) with one of the following reagents:
   a. DTT at 5 mM
   b. DTT at 50 mM
   c. DTT at 100 mM
   d. Trimethylamine N-oxide dehydrate at 3M
   e. Tris(2-carboxyethyl)phosphine hydrochloride at 10 mM These reagents were dissolved in a buffer of 200 μM HEPES, 100 mM NaCl, 10% Tween®20, 1 mM $ZnCl_2$. Of these choices, 100 mM DTT was found to give the highest sensitivity of the potency assay;
2. The reduced BoNT/A was serially diluted in a 200 mM HEPES buffer at pH 7.4, from 3000 U/ml down to 5 U/ml;
3. Reporter 1 was added to the serial diluted toxin plates or tubes containing purified Reporter 1 protein;
4. The plates/tubes were incubated for 4-22 hours at 20° C., 30° C., or 37° C., and of these combinations of time and temperature, 20° C. for 22 hours gave the highest sensitivity and was used for further studies; and
5. Performed Western blot with and Anti-c-Myc antibody (Sigma Aldrich) as a primary antibody to detect amount of cleaved Reporter 1 protein (see FIG. 7)

The Western blot protocol used is briefly described as follows: All the samples analyzed with Western Blot (WB) were diluted (1:1) in sample buffer [95% 2× Laemmli Sample Buffer (Bio-Rad #1610737), 5% 2-mercaptoethanol (Sigma-Aldrich #M3148)], and they were subsequently incubated on Thermo Cell Cooling & Heating Block (BIOER) at 95° C. for 5 minutes, to denature the proteins. After proteins were denatured, 10 μl of each sample were loaded to each well of 4-20% Mini-PROTEAN® TGX™ Precast Protein Gels, 15-well, 15 μl (Bio-Rad #4561096). The electrophoresis was run using Mini-PROTEAN® Tetra Vertical Electrophoresis Cell for Mini Precast Gels (Bio-Rad #1658004) (150 V, 90 minutes). 1× Tris/Glycine/SDS (TGS) Running Buffer [1:10 dilution of 10×TGS (Bio-Rad 1610732) to MQ $H_2O$] was used. A ladder [Precision Plus Protein™ Dual Color Standards (Bio-Rad #1610374)] was also loaded to the gel in order to be able to determine that the protein present in the samples is actually SNAP-25 (25 kDa).

When the electrophoresis was finished, Trans Blot® Turbo™ Mini PVDF Transfer Pack (Bio-Rad #1704156) and Trans Blot® Turbo™ Transfer System (Bio-Rad #1704150) were used to mediate protein migration from the gel to the membrane. The Transfer System was set at 2.5 A, 25V for a 3-minute run.

After the transfer was performed, pre-blocking of the membrane was conducted. The latter, was submerged in 25% EveryBlot Blocking Buffer (Bio-Rad #12010020). The blocking buffer was prepared by mixing 25% EveryBlot Blocking Buffer and 75% 1×TBS {1:10 dilution of 10×TBS [1.5 M NaCl, 0.4 M Trizma® HCL (Sigma-Aldrich #T5941) 0.1 M Trizma® Base (Sigma-Aldrich #T6066)] in MQ H2O}. The membrane was incubated in the blocking buffer for 1 hour, at room temperature, on gentle agitation (30 rpm, 0.5 degrees angle). This step was required to prevent primary antibody from binding to the membrane.

After blocking, the membrane was incubated with the primary antibody. Different primary antibodies were used in order to achieve the optimum detection: SNAP-25 antibody (Sigma-Aldrich #S9684 lot. No. O69M4872V) (1:1000 dilution in 25% EveryBlot Blocking Buffer), Myc Tag Monoclonal Antibody (Invitrogen #R950-25 lot. No. 1962274) (1:2500), and Myc-Tag Antibody (Cell Signaling #2272S lot. No. 6) (1:1000). The membrane was placed in a reaction folder with the primary antibody solution, and it was incubated overnight, on agitation (100 rpm), at 4° C.

The following day, the membrane was removed from the reaction folder, the primary antibody solution was discarded, and the membrane was washed for 10 minutes with 1×TTBS (1×TBS with 0.05% Tween®20) to remove unbound or non-specifically bound antibody. This step was repeated four times. During the washes, the membrane was being slightly agitated (30 rpm, 0.5 degrees angle).

The membrane was subsequently incubated for 1 hour with the secondary antibody solution, at room temperature, on gentle agitation (30 rpm, 0.5 degrees angle). Different secondary antibodies were used depending on the organization that the primary antibody derived from: anti-rabbit HRP-coupled secondary antibody (produced at the lab, lot. No. UK292785) (1:5000), HRP-goat anti-mouse secondary antibody (Invitrogen #626520 lot. No. 1324683A) (1:5000).

After the secondary antibody solution was discarded, the membrane was washed three times, as described above, and the development solution [Clarity™ Western ECL Substrate (Bio-Rad #1705060)] was added (1:1 Clarity™ Western Peroxide Reagent: Clarity™ Western Luminol/Enhancer Reagent). The blots were scanned on the CCD camera, using the Image Lab Software, provided by Bio-Rad. The percentage of SNAP-25 cleavage was quantified using the same software.

Figures 7, 8:
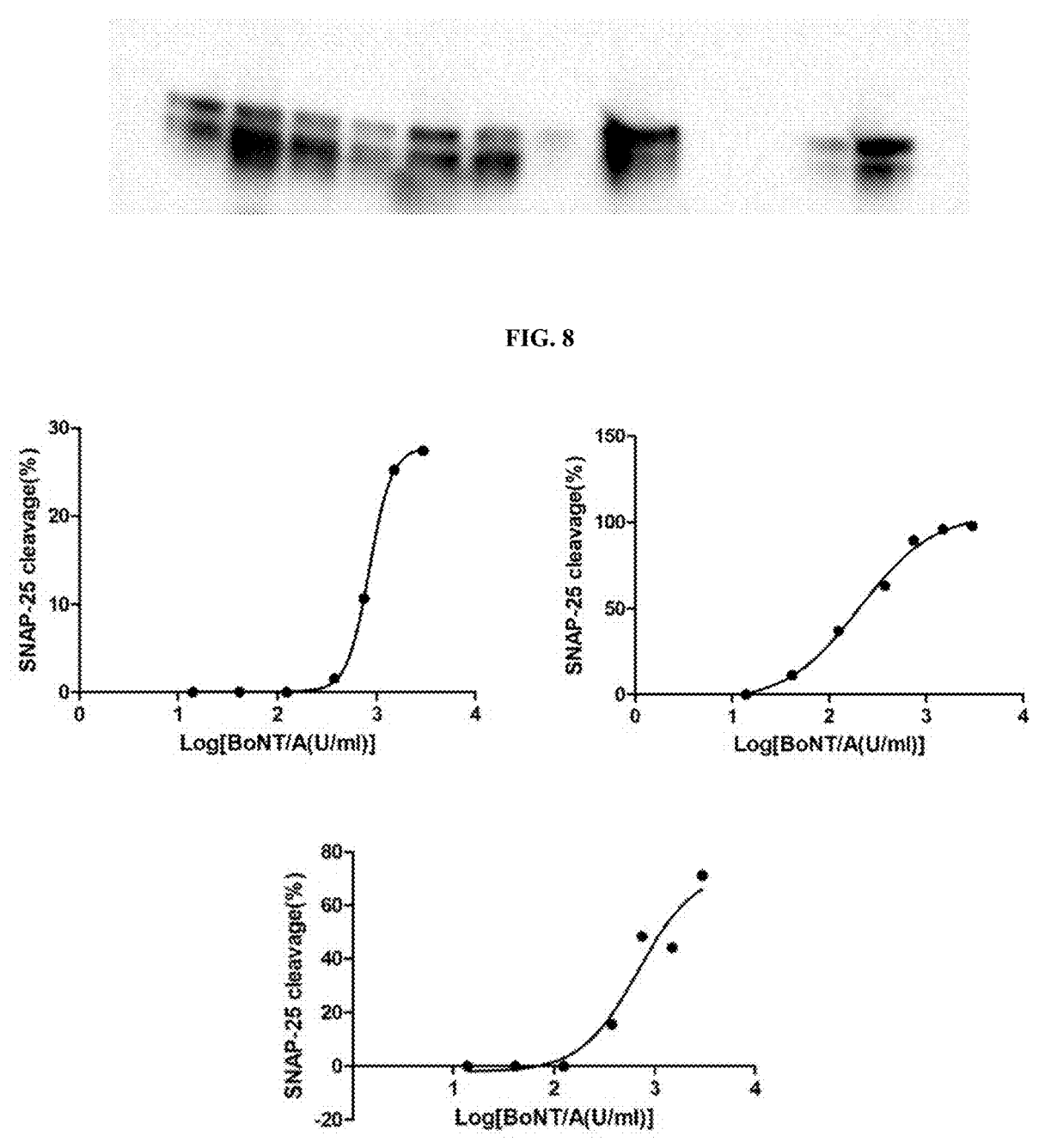

The resulting data was analyzed and is presented as a 4PL regression curve in FIG. 8. The data obtained here shows that incubation at 20° C. for 22 h gave the lowest $EC_{50}$ value (i.e. the highest sensitivity) at 204.5 U/ml QM-1114 concentration (see FIG. 8).

The analysis was further repeated but Western blot as detection method was replaced with a sandwich ELISA designed to detect only non-cleaved Reporter1 protein. The following protocol for sandwich ELISA was used:

c-Myc Monoclonal Antibody (9E11) (Invitrogen #MA-116637 lot. No. TL2685832A) was diluted 1:1000 into 10 mM Phosphate Buffered Saline (Gibco™ #18912014). The mix was used as a coating solution for Pierce™ 96-well Polystyrene Plates, White Opaque (Thermo Fisher Scientific #15042). After the coating solution (100 µl) had been added to each well, the plate was covered with adhesive plastic and it was incubated, overnight, at 4° C., on gentle agitation (100 rpm).

The following day, the coating solution was removed, and the plate was washed with PBS-T (10 mM PBS+0.05% Tween®20) to remove unbound antibodies. PBS-T (200 µl) was added to each coated well, and this step was repeated twice. The plate was subsequently blocked using Super-Block™ (PBS) Blocking Buffer (Thermo Fisher Scientific #37515). The blocking was performed according to manufacturer's instructions. This step was required in order to prevent SNAP-25 of the protein samples from binding to the wells. After blocking, the plate was washed twice with PBS-T, as described above, to remove any excess of blocking buffer. SNAP-25 samples (100 µl of each), diluted in 10 mM PBS (dilution depending on SNAP-25 concentration in the initial reaction sample), were loaded to all coated wells. Negative controls were also run; PBS without any protein sample was loaded instead. The plate was covered with adhesive plastic and it was incubated, overnight, at 4° C., on gentle agitation (100 rpm).

The following day, the sample solution was discarded and the plate was washed twice with PBS-T, as described above, to remove any excess of unbound SNAP-25. Subsequently, 100 µl of detection antibody diluted in PBS-T were added to each well. Detection antibody was diluted in PBS-T instead of PBS, because Tween®20 prevents the former from binding to the plate. Two different detection antibodies were used: Monoclonal anti-FLAG® M2-Peroxidase (HRP) antibody produced in mouse (Sigma-Aldrich #A-8592 lot. No. 061K92201) (1:20000 dilution in PBS-T), SNAP-25 antibody (Sigma-Aldrich #S9684 lot. No. 069M4872V) (1:1500). The plate was covered with adhesive plastic and it was incubated on gentle agitation (80 rpm), at room temperature, for 2 hours.

In cases where the SNAP-25 antibody was used, an anti-rabbit HRP-coupled secondary antibody (produced at the lab, lot. No. UK292785) was also required. Therefore, after the detection antibody solution was removed, the plate was washed four times with PBS-T, and 100 µl of the secondary antibody, diluted 1:10000 in PBS-T, were added to each well. The plate was incubated for 1.5 hour, at room temperature, on gentle agitation (80 rpm). In cases were the HRP-coupled anti-FLAG antibody was used, a further secondary antibody incubation was not required.

During the last step, the antibody solution was removed, the plate was washed four times with PBS-T, to remove unbound antibody, or antibody that was bound to the plate, and 100 µl of the development solution [SuperSignal™ ELISA Pico Chemiluminescent Substrate (Thermo Fisher Scientific #37069)] were added to each well (1:1 SuperSignal™ ELISA Pico Stable Peroxide Solution: SuperSignal™ ELISA Pico Luminol/Enhancer Solution). It was important to wash the plate properly during this step, otherwise nonspecifically bound antibody would have interfered with the results. The plate was analyzed using Omega Microplate Reader (BMG LABTECH) and the results were given to measured Relative Luminescent Units (RFU).

Figure 9:
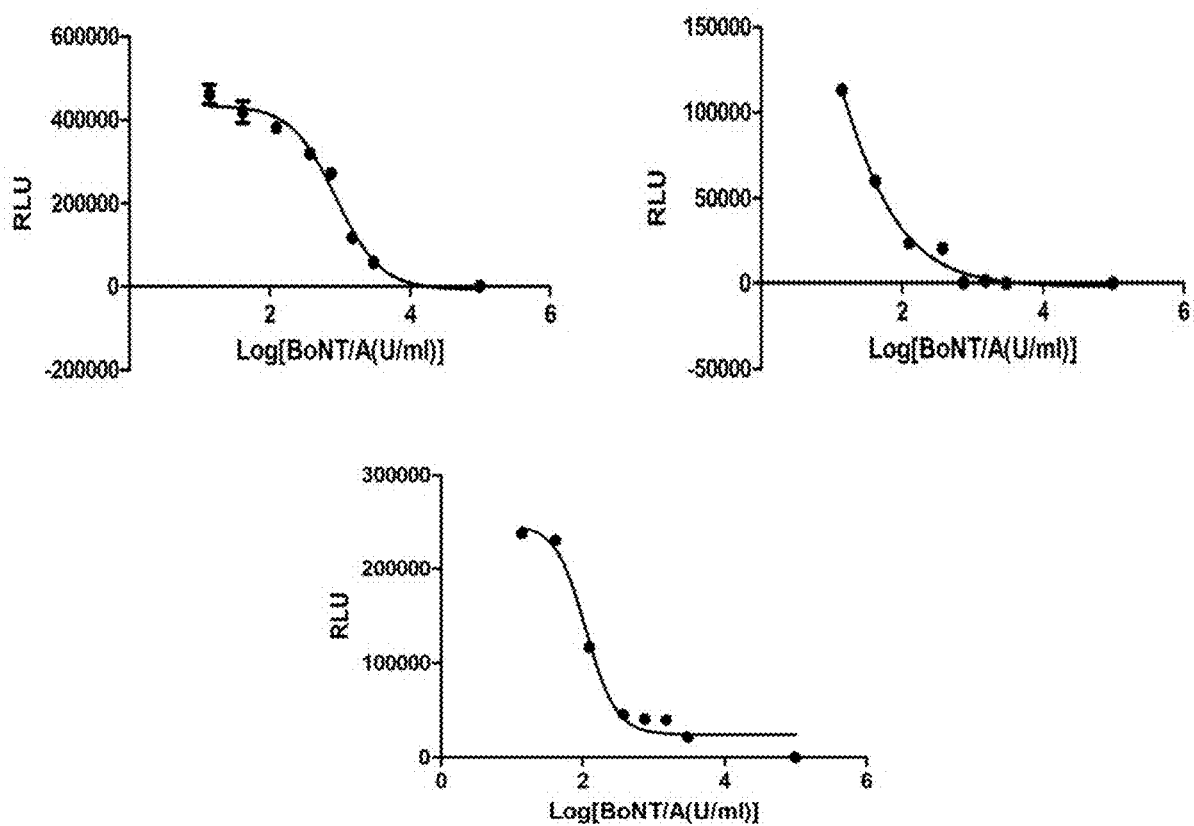
FIG. 9 shows dose-response [log(agonist) vs. response-non-linear regression] curves indicating the estimated amount of uncleaved product given in Relative Luminescent Units (RLU). Panel A shows measured RLU in samples incubated for 4 hours at ambient temperature $R^2=0.9779$ EC50=880. Panel B shows estimated RLU in reaction samples incubated for 22 hours at room temperature. $R^2=0.9887$ EC50=55.26. Panel C shows RLU measured in samples incubated for 22 hours at 37° C. $R^2=0.9818$ EC50=111.5. A value of known response (x value=5, y value=0) was added to every data set for curve fit optimization. Y axis values were adjusted according to the highest number of RLU measured in every group of samples.

This ELISA detection method increased sensitivity to an $EC_{50}$ of 55.56 U/ml QM-1114 concentration (see FIG. 9).

All patents and publications mentioned in the specification are indicative of the levels of those of ordinary skill in the art to which the disclosure pertains. All patents and publications are herein incorporated by reference to the same extent as if each individual publication was specifically and individually indicated to be incorporated by reference.

Further, one skilled in the art readily appreciates that the present disclosure is well adapted to carry out the objects and obtain the ends and advantages mentioned, as well as those inherent therein. Modifications therein and other uses will occur to those skilled in the art. These modifications are encompassed within the spirit of the disclosure and are defined by the scope of the claims, which set forth non-limiting embodiments of the disclosure.

What is claimed:

1. A peptide reporter comprising an amino acid sequence comprising amino acids 2-224 of SEQ ID NO: 9; amino acids 2-231 of SEQ ID NO: 10; amino acids 2-222 of SEQ ID NO: 11; amino acids 2-224 of SEQ ID NO: 12; or amino acids 2-215 of SEQ ID NO: 13.

2. The peptide of claim 1, wherein the peptide comprises any one of SEQ ID NOs: 9, 10, 11, 12, or 13.

3. The peptide of claim 1, wherein the peptide comprises an amino acid sequence consisting of amino acids 2-224 of SEQ ID NO: 9; amino acids 2-231 of SEQ ID NO: 10; amino acids 2-222 of SEQ ID NO: 11; amino acids 2-224 of SEQ ID NO: 12; or amino acids 2-215 of SEQ ID NO: 13.

4. The peptide of claim 1, wherein the SNAP-25 domain can be cleaved by BoNT/A, BONT/B, BONT/C, BONT/D, BONT/E, BONT/F, or BoNT/G.

5. A method of determining the enzymatic activity of a sample containing a *botulinum* neurotoxin (BoNT) comprising, contacting the sample containing a BONT with the peptide of claim 1 and determining whether the peptide was cleaved.

6. The method of claim 5, wherein determining whether the peptide was cleaved is established by contacting the peptide with a substrate comprising a capture antibody that specifically binds to one of the at least two additional domains, contacting the bound peptide with a second labeled antibody that specifically binds to a different domain than the capture antibody, washing the bound antibody to remove any unbound labeled antibody, and detecting the signal, if any, of the labeled antibody.

7. The method of claim 5, wherein determining whether the peptide was cleaved comprises utilizing an ELISA assay or flow cytometry.

8. The method of claim 5, wherein determining whether the peptide was cleaved is established by contacting a cell culture with the peptide and assessing whether the peptide induces apoptosis.

9. The method of claim 8, wherein the cell culture is in direct contact with the peptide and the BoNT.

10. The method of claim 8, wherein the peptide is introduced to the cell culture without the BoNT, but after a period of incubation with the BoNT.

11. The method of claim 8, wherein apoptosis is assessed by detecting or assessing at least one of caspase 3/7, caspase 8, caspase 9, DNA fragmentation, phosphatidylserine exposure, TUNEL staining, Annexin V staining, trypan blue permeability, lactate dehydrogenase, or a colorometric tetrazolium salt.

12. A method of assessing or quantifying *botulinum* neurotoxin (BoNT) activity comprising contacting a sample containing a BoNT with a SNAP-25 reporter construct according to claim 1, and determining whether the SNAP-25 reporter construct is cleaved by detecting the presence or absence of the at least two additional domains of the SNAP-25 reporter construct.

13. The method of claim 12, wherein determining whether the SNAP-25 reporter construct is cleaved comprises using an ELISA assay or flow cytometry.

14. A method of assessing or quantifying *botulinum* neurotoxin (BoNT) activity comprising contacting a sample containing a BoNT with a SNAP-25 reporter construct according to claim 1, and determining whether the SNAP-25 reporter construct is cleaved by assessing apoptosis in a cell culture that is contacted with the SNAP-25 reporter either after or during the reporter's contact with the BoNT.

15. The method of claim 14, wherein determining whether the SNAP-25 reporter construct is cleaved comprises using an apoptosis assay selected from the group consisting of a colorometric assay utilizing a tetrazolium salt, Annexin V and/or PI staining, a caspase activation assays, a phosphatidylserine localization assay, TUNEL staining, a lactate dehydrogenase localization assay, and trypan blue staining.

16. A kit comprising a peptide according to claim 1, wherein the kit optionally further comprises a capture antibody bound to a substrate and a detectably labeled antibody, wherein the capture antibody binds to the MYC domain and the detectably labeled antibody binds to the FLAG domain or wherein the capture antibody binds to the FLAG domain and the detectably labeled antibody binds to the MYC domain; wherein the kit optionally further comprises at least one apoptosis detection reagent selected from the group consisting of an anti-caspase 3 antibody, an anti-caspase 7 antibody, an anti-caspase 8 antibody, an anti-caspase 9 antibody, Annexin V, trypan blue, and a tetrazolium salt; and wherein the substrate is optionally a plate, a slide, or a bead.

17. A nucleic acid encoding a peptide according to claim 1, wherein the nucleic acid is optionally comprised within an expression vector.

18. A cell comprising the nucleic acid of claim 17, wherein the cell is optionally a mammalian cell or a human embryonic kidney cell (HEK).

19. The peptide of claim 1, wherein the peptide comprises amino acids 2-224 of SEQ ID NO: 9.

20. The peptide of claim 1, wherein the peptide comprises amino acids 2-231 of SEQ ID NO: 10.

21. The peptide of claim 1, wherein the peptide comprises amino acids 2-222 of SEQ ID NO: 11.

22. The peptide of claim 1, wherein the peptide comprises amino acids 2-224 of SEQ ID NO: 12.

23. The peptide of claim 1, wherein the peptide comprises amino acids 2-215 of SEQ ID NO: 13.

24. The peptide of claim 1, wherein the peptide comprises an amino acid sequence consisting of amino acids 2-224 of SEQ ID NO: 9.

25. The peptide of claim 1, wherein the peptide comprises an amino acid sequence consisting of amino acids 2-231 of SEQ ID NO: 10.

26. The peptide of claim 1, wherein the peptide comprises an amino acid sequence consisting of amino acids 2-222 of SEQ ID NO: 11.

27. The peptide of claim 1, wherein the peptide comprises an amino acid sequence consisting of amino acids 2-224 of SEQ ID NO: 12.

28. The peptide of claim 1, wherein the peptide comprises an amino acid sequence consisting of amino acids 2-215 of SEQ ID NO: 13.

* * * * *